(12) United States Patent
Medlock et al.

(10) Patent No.: US 10,047,019 B2
(45) Date of Patent: *Aug. 14, 2018

(54) EFFICIENT PROCESS OF ASYMMETRIC HYDROGENATION OF UNSATURATED KETONES USING ADDITIVES

(71) Applicant: DSM IP ASSETS B.V., Heerlen (NL)

(72) Inventors: Jonathan Alan Medlock, Kaiseraugst (CH); Gerardus Karel Maria Verzijl, Kaiseraugst (CH); Edwin Gerard Ijpeij, Kaiseraugst (CH); Andreas Hendrikus Maria De Vries, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/651,505

(22) PCT Filed: Dec. 18, 2013

(86) PCT No.: PCT/IB2013/061081
§ 371 (c)(1),
(2) Date: Jun. 11, 2015

(87) PCT Pub. No.: WO2014/097170
PCT Pub. Date: Jun. 26, 2014

(65) Prior Publication Data
US 2015/0321971 A1    Nov. 12, 2015

(30) Foreign Application Priority Data

Dec. 18, 2012 (EP) .................................... 12197791

(51) Int. Cl.
| | |
|---|---|
| *C07C 45/62* | (2006.01) |
| *C07B 35/02* | (2006.01) |
| *C07D 311/72* | (2006.01) |
| *C07B 53/00* | (2006.01) |

(52) U.S. Cl.
CPC .............. *C07B 35/02* (2013.01); *C07B 53/00* (2013.01); *C07C 45/62* (2013.01); *C07D 311/72* (2013.01); *C07B 2200/07* (2013.01)

(58) Field of Classification Search
None
See application file for complete search history.

(56) References Cited

FOREIGN PATENT DOCUMENTS

| | | | |
|---|---|---|---|
| WO | WO 2006/066863 | 6/2006 | |
| WO | WO 2012171969 A1 * | 12/2012 | ............. C07C 45/62 |

OTHER PUBLICATIONS

Vogl, Erasmus. Angew. Chem. Int. Ed. (1999) 38, 1570-1577.*
Wang, Duo-Sheng. Tetrahedron Letters 51 (2010) 3014-3017.*
Reichardt, Christian. Solvents and Solvent Effects in Organic chemistry. 3rd ed. Wiley-VCH (2003) 418-421.*
International Search Report for PCT/IB2013/061081 dated Mar. 3, 2014, four pages.
Woodmansee et al., "Chiral pyridyl phosphinites with large aryl substituents as efficient ligands for the asymmetric iridium-catalyzed hydrogenation of difficult substrates", *Chemical Science*, vol. 1, May 12, 2010, pp. 72-78.

* cited by examiner

*Primary Examiner* — Deepak R Rao
*Assistant Examiner* — Laura M Daniel
(74) *Attorney, Agent, or Firm* — Nixon & Vanderhye P.C.

(57) ABSTRACT

The present invention relates to a process of the asymmetric hydrogenation of an unsaturated ketone or aldehyde by molecular hydrogen in the presence of at least one chiral iridium complex and in the presence of at least one additive and a halogenated alcohol. This process yields chiral compounds in a very efficient way and is very advantageous in that the amount of iridium complex can be remarkably reduced.

8 Claims, No Drawings

EFFICIENT PROCESS OF ASYMMETRIC HYDROGENATION OF UNSATURATED KETONES USING ADDITIVES

This application is the U.S. national phase of International Application No. PCT/IB2013/061081 filed 18 Dec. 2013 which designated the U.S. and claims priority to EP Patent Application No. 12197791.2 filed 18 Dec. 2012, the entire contents of each of which are hereby incorporated by reference.

TECHNICAL FIELD

The present invention relates to the field of asymmetric hydrogenations of unsaturated compounds.

BACKGROUND OF THE INVENTION

Chiral compounds are important products and intermediates in different fields of application, particularly in the field of pharma, food supplements and flavours and fragrances as different stereoisomers have strongly different properties. A very important class of chiral compounds are chiral ketones and aldehydes.

Particularly important are chiral ketones for the synthesis of aroma ingredients and for vitamins, particular for tocopherol and vitamin K1.

Natural tocopherols bear a side chain having 3 stereogenic centres of the R configuration. Synthetic routes for the synthesis of (2R,4'R,8'R)-α-tocopherol are possible starting from (R,R)-isophytol or (R,R)-phytol. However, as natural sources of (2R,4'R,8'R)-tocopherols and (R,R)-phytol, are very limited, the market has a strong need for an effective synthesis of (2R,4'R,8'R)-tocopherols and (R,R)-isophytol, respectively, and chiral ketones or aldehydes are important intermediates for their synthesis.

It is known that chiral ketones are accessible from asymmetric hydrogenation of unsaturated ketones using chiral transition metal complexes. An important class of chiral transition metal complexes are chiral iridium complexes.

For example WO 2006/066863 A1 discloses a specific class of chiral iridium complexes which are suitable for the asymmetric hydrogenation of alkenes showing high stereoselectivity in the formation of hydrogenated ketones at high conversion. However, the iridium complexes need to be used in a relatively high amount relative to the unsaturated compounds to be hydrogenated. Due to the high price of iridium complexes it is commercially interesting to use as little iridium complex as possible while maintaining high conversion and good stereoselectivity.

SUMMARY OF THE INVENTION

Therefore, the problem to be solved is to offer a system for increasing the efficiency of iridium complexes in an asymmetric hydrogenation by molecular hydrogen.

Surprisingly it has been found that this problem can be solved by embodiments of the invention as disclosed herein.

This processes lead to the possibility that significantly lower amounts of chiral iridium complex can be used as compared to the known methods and whilst still obtaining the high conversion and high stereoselectivity.

Further aspects of the invention are subject of further independent claims. Particularly preferred embodiments are subject of dependent claims.

DETAILED DESCRIPTION OF THE INVENTION

In a first aspect the present invention relates to a process of manufacturing compounds of formula (I-A) or (II-A) by asymmetric hydrogenation of an unsaturated ketone or unsaturated aldehyde of the formula (I) or (II) with molecular hydrogen in the presence of at least one chiral iridium complex and in the presence of at least one additive and a halogenated alcohol

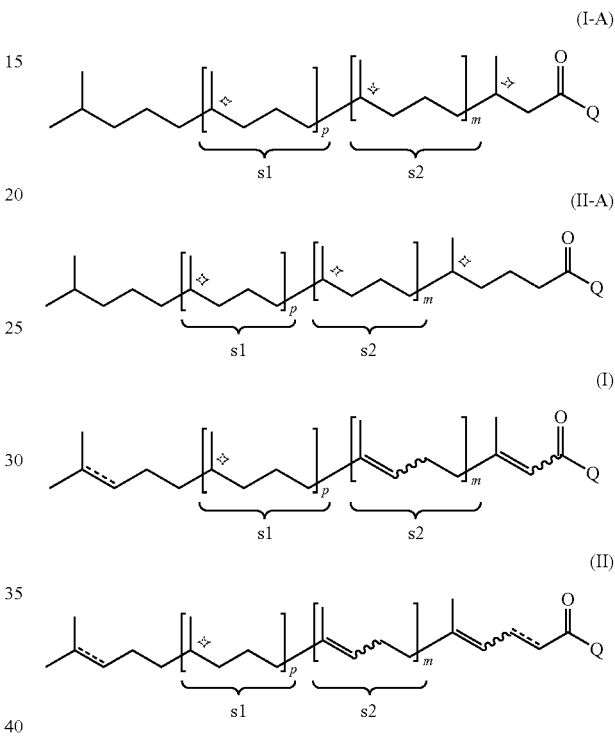

wherein Q stands for H or $CH_3$ and m and p stand independently from each other for a value of 0 to 3 with the proviso that the sum of m and p is 0 to 3, and where a wavy line represents a carbon-carbon bond which is linked to the adjacent carbon-carbon double bond so as to have said carbon-carbon double either in the Z or in the E-configuration and where the substructures in formula (I) and (II) represented by s1 and s2 can be in any sequence; and wherein the double bond having dotted line (=====) in formula (I) and (II) represents either a single carbon-carbon bond or a double carbon-carbon bond;

and wherein ✧ represents a stereogenic centre;

and wherein the additive is selected from the group consisting of organic sulfonic acids, transition metal salts of organic sulfonic acids, metal alkoxides, aluminoxanes, alkyl aluminoxanes and $B(R)_{(3-v)}(OZ)_v$;

wherein v stands for 0, 1, 2 or 3 and

R stands for F, a $C_{1-6}$-alkyl, a halogenated $C_{1-6}$-alkyl, an aryl or halogenated aryl group; and Z stands for a $C_{1-6}$-alkyl, a halogenated $C_{1-6}$-alkyl, an aryl or halogenated aryl group.

The sum of m and p is preferably 0 to 2, particularly 0 or 1.

The term "independently from each other" in this document means, in the context of substituents, moieties, or groups, that identically designated substituents, moieties, or groups can occur simultaneously with a different meaning in the same molecule.

A "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —CH(CH$_3$)—CH$_2$—CH$_3$ is considered as a $C_4$-alkyl group.

A "$C_{x-y}$-alkylene" group is an alkylene group comprising x to y carbon atoms, i.e., for example $C_2$-$C_6$ alkylene group is an alkyl group comprising 2 to 6 carbon atoms. The alkylene group can be linear or branched. For example the group —CH(CH$_3$)—CH$_2$— is considered as a $C_3$-alkylene group.

A "phenolic alcohol" means in this document an alcohol which has a hydroxyl group which is bound directly to an aromatic group.

Substance names starting with "poly" as used in the present document refer to substances formally containing two or more of the corresponding functional groups per molecule.

The term "stereogenic centre" as used in this document is an atom, bearing groups such that interchanging of any two of the groups leads to a stereoisomer. Stereoisomers are isomeric molecules that have the same molecular formula and sequence of bonded atoms (constitution), but that differ in the three-dimensional orientations of their atoms in space.

The configuration at a stereogenic centre is defined to be either R or S. The R/S-concept and rules for the determination of the absolute configuration in stereochemistry is known to the person skilled in the art.

In the present document a carbon-carbon double bond is defined as being "prochiral" if addition of molecular hydrogen to said carbon-carbon double bond leads to the formation of a stereogenic carbon centre.

Cis/trans isomers are configurational isomers having different orientation at the double bond. In this document the term "cis" is equivalently used for "Z" and vice versa as well as "trans" for "E" and vice versa. Therefore, for example the term "cis/trans isomerization catalyst" is equivalent to the term "E/Z isomerization catalyst".

A "cis/trans isomerization catalyst" is a catalyst which is able to isomerize a cis isomer (Z-isomer) to a cis/trans isomer mixture (E/Z isomer mixture) or to isomerize a trans isomer (E-isomer) to a cis/trans isomer (E/Z isomer mixture).

The terms "E/Z", "cis/trans" and "R/S" denote mixtures of E and Z, of cis and trans, and of R and S, respectively.

The term "isomerization" or "isomerize" is to be understood as being limited to cis/trans isomerization in the whole document.

The terms "E/Z", "cis/trans" and "R/S" denote mixtures of E and Z, of cis and trans, and of R and S, respectively.

A "completely saturated" ketone or aldehyde is an unsaturated ketone or aldehyde, in which all carbon-carbon double bonds have been hydrogenated by asymmetric hydrogenation.

An "unsaturated ketone" or "unsaturated aldehyde" in this document ketone is defined as to be a ketone or aldehyde which is olefinically unsaturated, i.e. that it has at least one carbon-carbon double bond in its chemical structure, and which has at least one prochiral carbon-carbon double bond.

"Assay yield" of an asymmetric hydrogenation is in the present application the molar ratio of number of molecules of completely saturated ketones or aldehydes to the number of molecules of unsaturated ketones or aldehydes being submitted to the hydrogenation.

The term "(R,R)-isophytol" used in this document means (3RS,7R,11R)-3,7,11,15-tetramethylhexadec-1-en-3-ol).

The term "(R,R)-phytol" used in this document means (2E,7R,11R)-3,7,11,15-tetramethyl-2-hexadecen-1-ol).

In case identical labels for symbols or groups are found in several formulae, in the present document, the definition of said group or symbol made in the context of one specific formula applies also to other formulae which comprises said same label.

In the present document any single dotted line represents the bond by which a substituent is bound to the rest of a molecule.

Unsaturated Ketone or Aldehyde

The process of manufacturing compound of formula (I-A) or (II-A) uses unsaturated ketone or unsaturated aldehyde of the formula (I) or (II) as starting material. The compound of formula (I) or (II) have prochiral carbon-carbon double bonds.

Most preferably the compound of formula (I) or (II) is selected from the group consisting of 3,7-dimethyloct-6-enal, 3,7-dimethylocta-2,6-dienal, 3,7-dimethyloct-2-enal, 6,10-dimethylundeca-3,5,9-trien-2-one, 6,10-dimethylundeca-5,9-dien-2-one, 6,10-dimethylundec-5-en-2-one, 6,10-dimethylundec-3-en-2-one, 6,10-dimethylundec-3,5-diene-2-one, 6,10,14-trimethylpentadeca-5,9,13-trien-2-one, 6,10,14-trimethylpentadeca-5,9-dien-2-one, 6,10,14-trimethylpentadec-5-en-2-one and (R)-6,10,14-trimethylpentadec-5-en-2-one as well as all their possible E/Z-isomers.

Particularly preferred is compounds of (II), particularly being selected from the group consisting of 6,10-dimethylundeca-3,5,9-trien-2-one, 6,10-dimethylundeca-5,9-dien-2-one, 6,10-dimethylundec-5-en-2-one, 6,10-dimethylundec-3-en-2-one, 6,10-dimethylundec-3,5-diene-2-one, 6,10,14-trimethylpentadeca-5,9,13-trien-2-one, 6,10,14-trimethylpentadeca-5,9-dien-2-one, 6,10,14-trimethylpentadec-5-en-2-one and (R)-6,10,14-trimethylpentadec-5-en-2-one as well as all their possible E/Z-isomers.

Most preferably the compound of formula (I) or (II) is a ketone.

In case the unsaturated ketone or unsaturated aldehyde of the formula (I) or (II) has in the same molecule more than one prochiral carbon-carbon double bonds, such compounds may have the same ("all Z" or "all E") E/Z configurations or have different E/Z configurations (e.g. EZ or ZE). For the purpose of this invention, it is advisable that only those isomers of formula (I) or (II) having the E-configuration at all prochiral carbon-carbon double bonds and only those isomers of formula (I) or (II) having the Z-configuration at all prochiral carbon-carbon double bonds are subjected to the asymmetric hydrogenation. It is preferred that compounds of formula (I) or (II) which have in the same molecule different E/Z configurations at the prochiral carbon-carbon double bonds are submitted to a step of cis/trans isomerization of said prochiral carbon-carbon double bonds. Such a cis/trans isomerization is performed in the presence of a cis/trans isomerization catalyst, particularly an organic sulphur compound, particularly a polythiol, or nitrogen monoxide. This allows that undesired isomers are converted into such isomers having all E or all Z configuration at the corresponding prochiral double bonds.

Additive

The asymmetric hydrogenation is taken place in the presence of at least one additive. The additive is selected from the group consisting of organic sulfonic acids, transition metal salts of organic sulfonic acids, metal alkoxides, aluminoxanes, alkyl aluminoxanes and $B(R)_{(3-v)}(OZ)_v$, wherein v stands for 0, 1, 2 or 3 and R stands for F, a $C_{1-6}$-alkyl, a halogenated $C_{1-6}$-alkyl, an aryl or halogenated aryl group; and Z stands a $C_{1-6}$-alkyl, a halogenated $C_{1-6}$-alkyl, an aryl or halogenated aryl group.

Particularly suitable additives are selected from the group consisting of triflic acid, alkyl aluminoxanes, particularly methyl aluminoxane, ethyl aluminoxane, tetra alkoxy titanates, $B(R)_{(3-v)}(OZ)_v$; particularly tri-isopropylborate and triethylborane and $BF_3$, preferably in the form of a $BF_3$ etherate.

Particularly useful as the transition metal salts of organic sulfonic acids are scandium, indium, yttrium and zirconium salts of organic sulfonic acids.

Metal alkoxides are known to the person skilled in the art. This term particularly relates to the alkoxides of the elements of the group 4 and 13 of the periodic system. It is also known to the person skilled in the art that the metal alkoxides often do not form well-defined structures. Characteristically, metal alkoxides have hydrocarbyl group bound by an oxygen atom to a metal centre. A metal alkoxide may also have different metal centres which are bridged by oxygen or oxygen containing groups, such as for example (polynuclear)aluminium oxoalkoxides.

Particularly useful as metal alkoxides are titanium alkoxides (also being called alkoxy titanates) zirconium alkoxides (also being called alkoxy zirconates) or aluminium alkoxides.

A particularly preferred class of metal alkoxide is of the type of polynuclear aluminium oxoalkoxides such as disclosed in *J. Chem. Soc., Dalton Trans.*, 2002, 259-266 or in *Organometallics* 1993, 12, 2429-2431.

Alkyl aluminoxanes, are known products which are particularly useful as co-catalysts for olefin polymerizations of the Ziegler-Natta type. They are prepared by controlled hydrolysis of trialkylaluminium compound, particularly trimethylaluminium or triethylaluminium. The hydrolysis can be achieved for example by hydrated metal salts (metal salts containing crystal water).

Preferably the additive is selected from the group consisting of triflic acid, alkyl aluminoxanes, particularly methyl aluminoxane, ethyl aluminoxane, tetra alkoxy titanates, $B(R)_{(3-v)}(OZ)_v$; particularly tri-isopropyl borate and triethylborane and $BF_3$, preferably in the form of a $BF_3$ etherate.

More preferred are triflic acid, alkyl aluminoxanes, particularly methyl aluminoxane, ethyl aluminoxane, tetra alkoxy titanates, $B(R)_{(3-v)}(OZ)_v$; particularly tri-isopropyl borate and triethylborane.

Especially good results have been obtained by an additive with has been obtained from trimethylaluminoxane and 2,2,2-trifluoroethanol or from trialkylaluminium and 2,2,2-trifluoroethanol.

It has been found that the quality and speed of the asymmetric hydrogenation using molecular hydrogen in the presence of a chiral iridium complex is enhanced significantly when the above mentioned additives are used.

Halogenated Alcohol

The asymmetric hydrogenation is taken place in the presence of halogenated alcohol.

A preferred halogenated alcohol is a fluorinated alcohol, preferably a polyfluorinated alcohol, more preferably 2,2,2-trifluoroethanol.

Chiral Iridium Complex

The asymmetric hydrogenation is taken place in the presence of at least one chiral iridium complex.

Chiral iridium complexes are compounds having organic ligands being coordinated to a central iridium atom. The chirality of chiral iridium complexes is due to either the chirality of the ligands or the spacial arrangements of the ligands. This concept of chirality is well known from complex chemistry. Ligands can be monodentate or polydentate. Preferably, the ligands bound to the iridium central atom are chelating ligands.

For the present invention, it has been shown that particularly chiral iridium complexes having ligands bound to the iridium central atom and that exactly one of the ligands is an organic ligand bearing a stereogenic centre, particularly a chelating ligand bearing a stereogenic centre, are very suitable.

It is preferred that the chiral iridium complex is bound to a chelating organic ligand having N and P as coordinating atoms and to either two olefins or to a diene having two carbon-carbon double bonds, and that, hence, the chiral iridium complex has preferably the following formula (III-0)

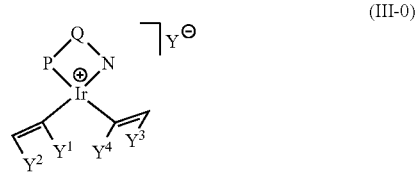

(III-0)

wherein

P-Q-N stands for a chelating organic ligand comprising a stereogenic centre or has planar or axial chirality and has a nitrogen and phosphorous atom as binding site to the iridium centre of the complex;

$Y^1$, $Y^2$, $Y^3$ and $Y^4$ are independently from each other hydrogen atoms, $C_{1-12}$-alkyl, $C_{5-10}$-cycloalkyl, or aromatic group; or at least two of them form together at least a two-valent bridged group of at least 2 carbon atoms; and $Y^\ominus$ is an anion, particularly selected from the group consisting of halide, $PF_6^-$, $SbF_6^-$, tetra(3,5-bis(trifluoromethyl)phenyl)borate ($BAr_F^-$), $BF_4^-$, perfluorinated sulfonates, preferably $F_3C$—$SO_3^-$ or $F_9C_4$—$SO_3^-$; $ClO_4^-$, $Al(OC_6F_5)_4^-$, $Al(OC(CF_3)_3)_4^-$, $N(SO_2CF_3)_2^-N(SO_2C_4F_9)_2^-$ and $B(C_6F_5)_4^-$.

The nitrogen and the phosphorous atom are preferably separated by 2 to 5, preferably 3, atoms in the chemical formula of the ligand P-Q-N.

The chelating organic ligand P-Q-N is preferably selected from the formulae (III-N1), (III-N2), (III-N3), (III-N4), (III-N5), (III-N6), (III-N7), (III-N8) and (III-N9)

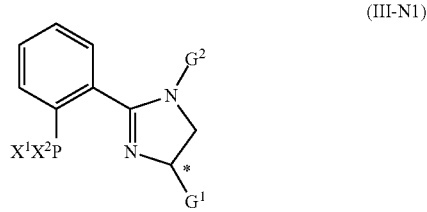

(III-N1)

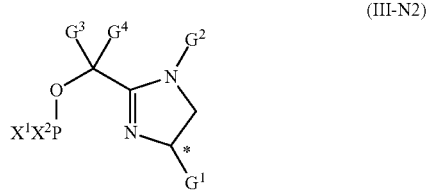

(III-N2)

-continued (III-N3) 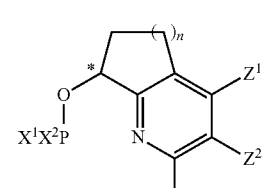

(III-N4) 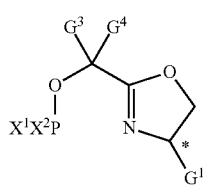

(III-N5) 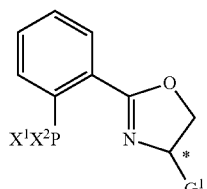

(III-N6) 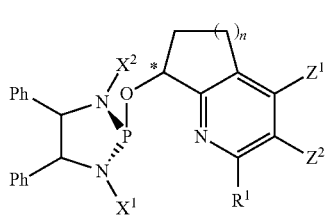

(III-N7) 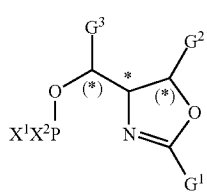

(III-N8) 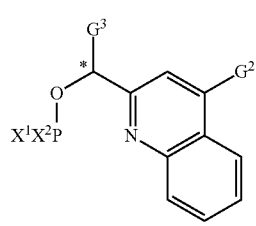

(III-N9) 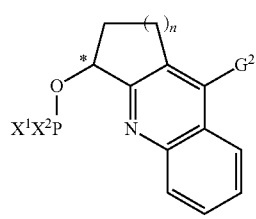

wherein $G^1$ represents either a $C_1$-$C_4$-alkyl, $C_{5-7}$-cycloalkyl, adamantyl, phenyl (optionally substituted with one to three $C_{1-5}$-alkyl, $C_{1-4}$-alkoxy, $C_{1-4}$-perfluoroalkyl groups and/or one to five halogen atoms)), benzyl, 1-naphthyl, 2-naphthyl, 2-furyl group;

$G^2$, $G^3$ and $G^4$ represent independently from each other hydrogen atoms or a $C_1$-$C_4$-alkyl, $C_{5-7}$-cycloalkyl, adamantyl, phenyl (optionally substituted with one to three $C_{1-5}$-, $C_{1-4}$-alkoxy, $C_{1-4}$-perfluoroalkyl groups and/or one to five halogen atoms)), benzyl, 1-naphthyl, 2-naphthyl, 2-furyl group;

$X^1$ and $X^2$ are independently from each other hydrogen atoms, $C_{1-4}$-alkyl, $C_{5-7}$-cycloalkyl, adamantyl, phenyl (optionally substituted with one to three $C_{1-5}$-alkyl, $C_{1-4}$-alkoxy, $C_{1-4}$-perfluoroalkyl groups and/or one to five halogen atoms)), benzyl, 1-naphthyl, 2-naphthyl, 2-furyl or ferrocenyl;

Ph stands for phenyl;

n is 1 or 2 or 3, preferred 1 or 2;

and $R^1$, $Z^1$ and $Z^2$ are as defined later for formula (III)

In case $Y^1$ and $Y^2$ and/or $Y^3$ and $Y^4$ form an olefin of the formula $Y^1$═$Y^2$ and/or of the Formula $Y^3$═$Y^4$, this olefin is or these olefins are preferably selected from the group consisting of ethene, prop-1-ene, 2-methylprop-1-ene, 2-methylbut-2-ene, 2,3-dimethylbut-2-ene, (Z)-cyclooctene, cyclohexene, cyclo-heptene, cyclopentene and norbornene.

In case $Y^1$, $Y^2$, $Y^3$ and $Y^4$ are forming a diene, it is either cyclic (double bond in a cycle) or acyclic (double bond not in a cycle).

The two carbon-carbon double bonds of the diene are preferably linked by two carbon bonds, i.e. the dienes preferably comprise the substructure C═C—C—C—C═C.

Examples of preferred acylic dienes are hexa-1,5-diene, hepta-1,5-diene, octa-1,5-diene, octa-2,6-diene, 2,4-dialkyl-2,7-octadiene, 3,6-dialkylocta-2,6-diene, 1,2-divinylcyclohexane and 1,3-butadiene.

Examples for cyclic dienes are cycloocta-1,5-diene, cyclohexa-1,4-diene, cyclohexa-1,3-diene, 3,4,7,8-tetraalkylcycloocta-1,5-diene, 3,4,7-trialkylcycloocta-1,5-diene, 3,4-di-alkylcycloocta-1,5-diene, 3,7-di-alkylcycloocta-1,5-diene, 3,8-di-alkylcycloocta-1,5-diene, 3-alkylcycloocta-1,5-diene; norbornadiene, 1-alkylnorbornadiene, 2-alkylnorbornadiene, 7-alkylnorbornadiene, dicyclopentadiene, cyclo-pentadiene and (1s,4s)-bicyclo[2.2.2]octa-2,5-diene.

Preferred diene is cycloocta-1,5-diene.

A highly preferred class of chiral iridium complexes are chiral iridium complexes of formula (III)

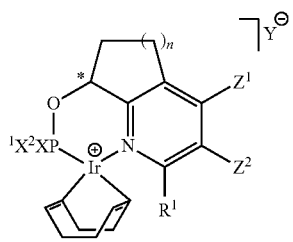

(III)

wherein n is 1 or 2 or 3, preferred 1 or 2;

$X^1$ and $X^2$ are independently from each other hydrogen atoms, $C_{1-4}$-alkyl, $C_{5-7}$-cycloalkyl, adamantyl, phenyl (optionally substituted with one to three $C_{1-5}$-, $C_{1-4}$-alkoxy, $C_{1-4}$-perfluoroalkyl groups and/or one to five halogen atoms)), benzyl, 1-naphthyl, 2-naphthyl, 2-furyl or ferrocenyl;

$Z^1$ and $Z^2$ are independently from each other hydrogen atoms, $C_{1-5}$-alkyl or $C_{1-5}$-alkoxy groups;

or $Z^1$ and $Z^2$ stand together for a bridging group forming a 5 to 6 membered ring;

$Y^\ominus$ is an anion, particularly selected from the group consisting of halide, $PF_6^-$, $SbF_6^-$, tetra(3,5-bis(trifluoromethyl)phenyl)borate ($BAr_F^-$), $BF_4^-$, perfluorinated sulfonates, preferably $F_3C\!-\!SO_3^-$ or $F_9C_4\!-\!SO_3^-$; $ClO_4^-$, $Al(OC_6F_5)_4^-$, $Al(OC(CF_3)_3)_4^-$, $N(SO_2CF_3)_2^-N(SO_2C_4F_9)_2^-$ and $B(C_6F_5)_4^-$;

$R^1$ represents either phenyl or o-tolyl or m-tolyl or p-tolyl or a group of formula (IVa) or (IVb) or (IVc)

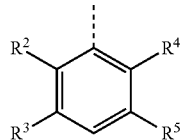
(IVa)

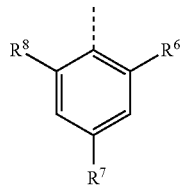
(IVb)

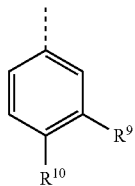
(IVc)

wherein $R^2$ and $R^3$ represent either both H or a $C_1$-$C_4$-alkyl group or a halogenated $C_1$-$C_4$-alkyl group or represent a divalent group forming together a 6-membered cycloaliphatic or an aromatic ring which optionally is substituted by halogen atoms or by $C_1$-$C_4$-alkyl groups or by $C_1$-$C_4$-alkoxy groups $R^4$ and $R^5$ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogens atoms or by $C_1$-$C_4$-alkyl groups or by $C_1$-$C_4$-alkoxy groups;

$R^6$ and $R^7$ and $R^8$ represent each a $C_1$-$C_4$-alkyl group or a halogenated $C_1$-$C_4$-alkyl group;

$R^9$ and $R^{19}$ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogens atoms or by $C_1$-$C_4$-alkyl groups or by $C_1$-$C_4$-alkoxy groups;

and wherein * represents a stereogenic centre of the complex of formula (III).

The complex of formula (III) is neutral, i.e. the complex consists of a complex cation of formula (III') and anion Y as defined before.

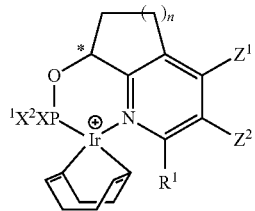
(III')

The person skilled in the art knows that anions and cations may be dissociated.

$X^1$ and/or $X^2$ represent preferably hydrogen atoms, methyl, ethyl, n-propyl, iso-propyl, n-butyl, iso-butyl, tert-butyl, n-pentyl, iso-pentyl, neopentyl, cyclopentyl, cyclohexyl, cycloheptyl, adamantly, phenyl, benzyl, o-tolyl, m-tolyl, p-tolyl, 4-methoxyphenyl, 4-trifluoromethylphenyl, 3,5-di-tert-butylphenyl, 3,5-dimethoxyphenyl, 1-naphthyl, naphthyl, 2-furyl, ferrocenyl or a phenyl group which is substituted with one to five halogen atoms.

In case of $X^1$ and/or $X^2$ representing phenyl groups which are substituted with one to five halogen atoms, the phenyl groups substituted by fluorine atoms are particularly useful, i.e. $C_6H_4F$, $C_5H_3F_2$, $C_5H_2F_3$, $C_5HF_4$ or $C_5F_5$.

In case of $X^1$ and/or $X^2$ representing phenyl groups which are substituted with one to three $C_{1-4}$-alkyl, the phenyl groups substituted by methyl group(s) are particularly useful, particularly ortho-tolyl and para-tolyl.

Preferably both $X^1$ and $X^2$ represent the same substituent.

Most preferred both $X^1$ and $X^2$ are phenyl or ortho-tolyl groups.

It is preferred that the $C_1$-$C_4$-alkyl or alkoxy groups used in the definition of $R^2$, $R^3$, $R^4$, $R^5$ $R^6$, $R^7$, $R^8$, $R^9$ and $R^{10}$ above are primary or secondary, preferably primary, alkyl or alkoxy groups.

A particularly suited substituent $R^1$ of formula (IVa) is the 9-anthryl or 1-naphthyl group.

A further particularly suited substituent $R^1$ of formula (IVb) is the mesityl group.

A further particularly suited substituent $R^1$ of formula (IVc) is the 2-naphthyl group.

Preferably $R^1$ is represented by phenyl (abbreviated as "Ph") or formula (IV-1) or (IV-2) or (IV-3), particularly (IV-1) or (IV-3).

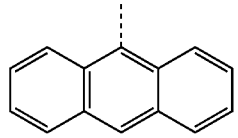
(IV-1)

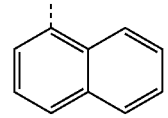
(IV-2)

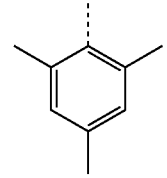
(IV-3)

abbreviated as "Anth" abbreviated as "1-Naphth" abbreviated as "Mes"

It has been found that the most preferred substituent $R^1$ is either 9-anthryl or phenyl.

The preferred chiral iridium complexes of formula (III) are the complexes of formulae (III-A), (III-B), (III-C), (III-D), (III-E) and (III-F).

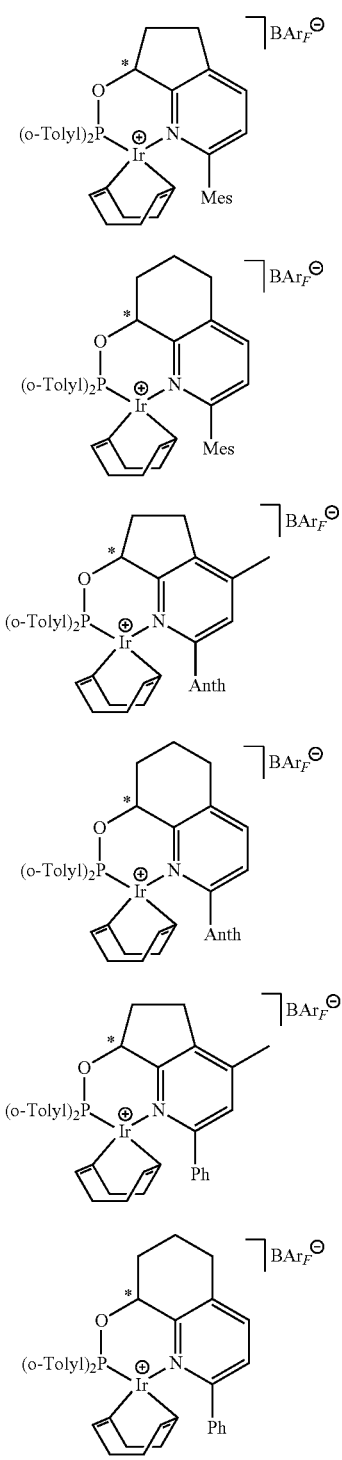

Most preferred as chiral iridium complexes of formula (III) are the complexes of formulae (III-C) and (III-D) and (III-F), particularly the one of formula (III-C) or (III-F).

The chiral iridium complexes of formula (III) can be synthesized accordingly as described in detail in *Chem. Sci.*, 2010, 1, 72-78 whose entire content is hereby incorporated by reference.

The iridium complex of formula (III) is chiral. The chirality at said chiral centre marked by the asterisk is either S or R, i.e. there exist two enantiomers (IIIa) and (IIIb) of the chiral complex of formula (III):

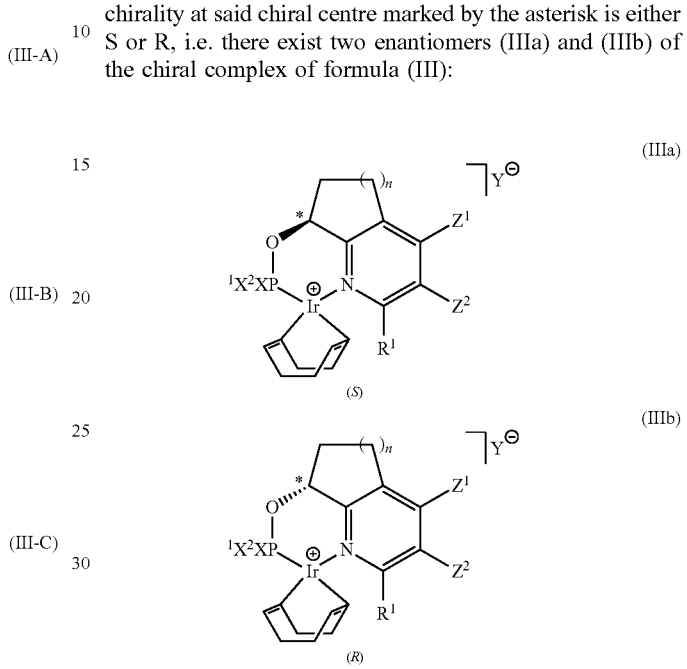

The individual enantiomers of the complex of formula (III) could be principally separated after the complexation step from a racemic mixture. However, as *Chem. Sci.*, 2010, 1, 72-78 discloses, the synthesis of the complex of formula (III) comprises a reaction involving a non-racemic chiral alcohol. As it is known that the further reaction steps do not modify the chirality of the complex its isomeric purity (S:R-ratio) is governed therefore by the enantiomeric purity of said alcohol. As said corresponding alcohol can be obtained in a R/S ratio of more than 99% resp. lower than 1%, the complex of formula (III) can be obtained in extremely high enantiomeric purities, particularly in a R/S ratio of more than 99% resp. lower than 1%.

The chiral iridium complex is preferably used in an excess of one enantiomer.

Particularly, it is preferred that the ratio of the molar amounts of the individual enantiomers R:S of the chiral iridium complex of formula (III) is more than 90:10 or less than 10:90, preferably in the range of 100:0 to 98:2 or 0:100 to 2:98. Most preferred is that this ratio is about 100:0 resp. about 0:100. The ultimately preferred ratio is 100:0 resp. 0:100.

In one embodiment the stereogenic centre indicated by * has the R-configuration.

In another embodiment the stereogenic centre indicated by * has the S-configuration.

Asymmetric Hydrogenation

The hydrogenating agent is molecular hydrogen ($H_2$). The hydrogenation can be carried out in substance (i.e. only unsaturated ketone or unsaturated aldehyde of the formula (I) or (II), chiral iridium complex, additive and halogenated alcohol)(neat) or in an inert carrier, particularly in an inert solvent, or a mixture of inert solvents. The hydrogenation is preferred carried out in substance Preferred suitable solvents are halogenated hydrocarbons, hydrocarbons, carbonates and ethers.

Particularly preferred solvents are hydrocarbons and halogenated hydrocarbons, particularly halogenated aliphatic hydrocarbons.

Preferred examples of hydrocarbons are hexane, heptane, toluene, xylene and benzene, particularly toluene and heptane.

Preferred ethers are dialkylethers. Particularly useful ethers are dialklyethers with less than 8 carbon atoms. Most preferred ether is methyl tert.-butyl ether ($CH_3$—O—C($CH_3)_3$).

One preferred group of halogenated hydrocarbon are halogenated aromatic compounds, particularly chlorobenzene.

Preferred examples of halogenated aliphatic hydrocarbons are mono- or polyhalogenated linear or branched or cyclic $C_1$— to $C_{15}$-alkanes. Especially preferred examples are mono- or polychlorinated or -brominated linear or branched or cyclic $C_1$— to $C_{15}$-alkanes. More preferred are mono- or polychlorinated linear or branched or cyclic $C_1$— to $C_{15}$-alkanes. Most preferred are dichloromethane, 1,2-dichloroethane, 1,1,1-trichloroethane, chloroform, and methylene bromide.

The most preferred solvent for the hydrogenation is dichloromethane.

The amount of solvent used is not very critical. However, it has been shown that the concentration of the ketone to be hydrogenated is preferably between 0.05 and 1 M, particularly between 0.2 and 0.7 M.

The hydrogenation reaction is conveniently carried out at an absolute pressure of molecular hydrogen from about 1 to about 100 bars, preferably at an absolute pressure of molecular hydrogen from about 20 to about 75 bars. The reaction temperature is conveniently between about 0 to about 100° C., preferably between about 10 to about 60° C.

The sequence of addition of the reactants and solvent is not critical.

The technique and apparatus suitable for the hydrogenation is principally known to the person skilled in the art.

By the asymmetric hydrogenation a prochiral carbon-carbon double bond is hydrogenated to form a chiral stereogenic centre at one or both of the carbon atoms.

As a basic rule the higher the amount of chiral iridium complex in view of the unsaturated ketone or of the unsaturated aldehyde of formula (I) or (II) is, the higher the yield of the desired product and the better the stereoselectivity is.

From a practical point of view it is preferred not more than 10 mol-%, more preferred not more than 6 mol-%, of the chiral iridium complex in view of the amount of the aldehyde or ketone to be hydrogenated.

However, in view of the high price of the chiral iridium complex it is desired to use as little amount of iridium complex as possible as long as the yield and the stereoselectivity in the hydrogenated product are acceptable. The threshold of acceptable is at that the desired stereoisomer is least 90% of all the isomers obtained and that the assay yield is at least 50%.

It has been observed that the asymmetric hydrogenation is possible at much lower amount of chiral iridium complex based on the amount of ketone aldehyde of formula (I) or (II) in the presence of additive and halogenated alcohol as compared to the corresponding ketone or aldehyde as such, i.e. without additive and/or halogenated alcohol. The indication of amount of chiral iridium complex may be given in mol-% based on the amount of the aldehyde or ketone. A different way of indicating the ratio of chiral iridium complex is the molar ratio of ketone or aldehyde to complex, which in the present document is indicated by S/C ("substrate to complex ratio")

It has been observed that even at amounts as low as 0.02 mol-% (S/C=5,000) in certain cases as low as 0.01 mol-% (S/C=10,000) a high yield of the hydrogenated ketone or aldehyde is still obtained in high stereoselectivity.

An S/C of more than 30,000, particularly more than 40,000 or more than 50,000 can be achieved. By optimizing the conditions even S/C of more than 100,000 or even 200,000 may be achieved.

Hence, the chiral iridium complex can be present during the hydrogenation in an amount in the range from 0.0001 to 5 mol-%, preferably from about 0.001 to about 2 mol-%, more preferably from about 0.001 to about 1 mol-%, most preferably from 0.002 to 0.1 mol-%, based on the amount of the aldehyde or ketone of formula (I) or (II).

When using a chiral iridium complex the prochiral carbon-carbon double bond is asymmetrically hydrogenated by molecular hydrogen. The complex of a specific absolute configuration yields a specific configuration of the stereogenic carbon centre being formed by the asymmetric hydrogenation.

It has been observed when using a chiral iridium complex of formula (III), that the chiral iridium complexes of formula (III) having the S-configuration at the stereogenic centre indicated by *, yield the R-configuration at the stereogenic centre being formed by the hydrogenation when the prochiral carbon-carbon double bond has the E-configuration, or yield the S-configuration at the stereogenic centre being formed by the hydrogenation when the prochiral carbon-carbon double bond has the Z-configuration.

On the other hand, when the chiral iridium complexes of formula (III) has the R-configuration at the stereogenic centre indicated by *, the hydrogenation of a prochiral carbon-carbon double bond having the Z-configuration yields the R-configuration at the stereogenic centre being formed by the hydrogenation and the hydrogenation of a prochiral carbon-carbon double bond having the E-configuration yields the S-configuration at the stereogenic centre being formed by the hydrogenation.

As particularly, it is preferred to have hydrogenation products having R-configuration at the stereogenic centres being formed it is preferred to use a chiral iridium complex of formula (III) having the S-configuration at the stereogenic centre indicated by * in the case where corresponding prochiral double bond of the unsaturated aldehyde or ketone has the E-configuration; or use a chiral iridium complexes of formula (III) having the R-configuration at the stereogenic centre indicated by * in the case where corresponding prochiral double bond of the unsaturated aldehyde or ketone has the Z-configuration.

It is further preferred that the additive is present in the range of 1 to 3000 mol additive per mol chiral iridium complex.

Hydrogenated Ketone or Aldehyde

As a result of the asymmetric hydrogenation the compound of formula (I-A) or (II-A) are formed.

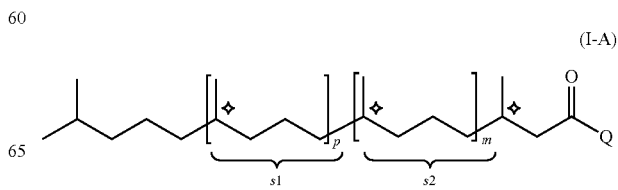

(I-A)

(II-A)

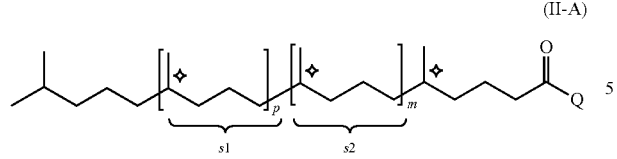

As a result of the asymmetric hydrogenation a ketone or aldehyde having at least one stereogenic carbon centre is formed. Said at least one stereogenic carbon centre is formed from a prochiral carbon-carbon double bond by the asymmetric hydrogenation of the unsaturated ketone or aldehyde.

Preferred compounds of formula (I-A) and (II-A) are (R)-3,7-dimethyloctanal, (R)-6,10-dimethylundecan-2-one and (6R,10R)-6,10,14-trimethylpentadecan-2-one.

The compounds of formula (I-A) or (II-A) formed by the described process is highly pure and has a high purity in view of the configuration at the stereogenic centres.

The compounds of formula (I-A) or (II-A) are interesting to be used in the fields of pharma, food supplements and flavours and fragrances or as intermediate products in the synthesis of substances, particularly for the synthesis of tocopherol or vitamin K1.

Particularly, the compound (6R,10R)-6,10,14-trimethylpentadecan-2-one is an important intermediate and is particularly useful for the synthesis of (R,R)-isophytol, (R,R)-phytol, (2-ambo)-α-tocopherol or of (2R,4'R,8'R)-α-tocopherol or vitamin K1.

In a further aspect the invention relates to a composition comprising
i) at least one unsaturated ketone or unsaturated aldehyde of the formula (I) or (II) as described above for the process of manufacturing compound of formula (I-A) or (II-A) in detail;
ii) at least one chiral iridium complex;
iii) at least one additive which is selected from the group consisting of organic sulfonic acids, transition metal salts of organic sulfonic acids, transition metal salts of organic sulfonic acids, metal alkoxides, aluminoxanes, alkyl aluminoxanes and $B(R)_{(3-\nu)}(OZ)_\nu$; as described above for the process of manufacturing compound of formula (I-A) or (II-A) in detail; and
iv) at least one halogenated alcohol as described above for the process of manufacturing compound of formula (I-A) or (II-A) in detail.

Particularly preferred is that the chiral iridium complex is an iridium complex having ligands bound to the iridium central atom and that exactly one of the ligands is an organic ligand bearing a stereogenic centre, particularly a chelating ligand bearing a stereogenic centre.

The chiral iridium complex is a chiral iridium complex of formula (III-0)

(III-0)

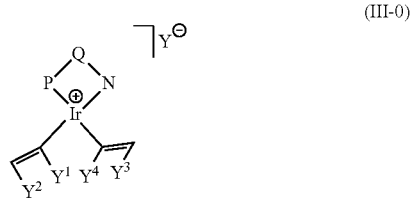

more preferably a chiral iridium complex of the formula (III)

(III)

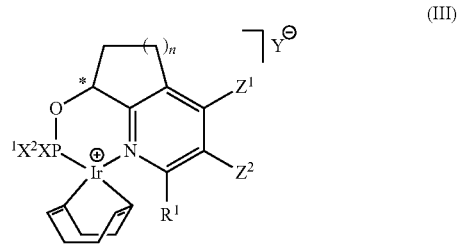

These chiral iridium complexes have already been discussed above in great detail.

The preferred unsaturated ketone or unsaturated aldehyde of the formula (I) or (II) are as described above selected from the group consisting of 3,7-dimethyloct-6-enal, 3,7-dimethylocta-2,6-dienal, 3,7-dimethyloct-2-enal, 6,10-dimethylundeca-3,5,9-trien-2-one, 6,10-dimethylundeca-5,9-dien-2-one, 6,10-dimethylundec-5-en-2-one, 6,10-dimethylundec-3-en-2-one, 6,10-dimethylundec-3,5-diene-2-one, 6,10,14-trimethylpentadeca-5,9,13-trien-2-one, 6,10,14-trimethylpentadeca-5,9-dien-2-one, 6,10,14-trimethylpentadec-5-en-2-one and (R)-6,10,14-trimethylpentadec-5-en-2-one as well as all their possible E/Z-isomers The additive is as discussed above preferably selected from the group consisting of triflic acid, alkyl aluminoxanes, particularly aluminoxanes, tetra alkoxy titanates, $B(R)_{(3-\nu)}(OZ)_\nu$; particularly tri-isopropyl borate and triethylborane and $BF_3$, preferably in the form of a $BF_3$ etherate.

The halogenated alcohol is as discussed above preferably 2,2,2-trifluoroethanol.

The composition can particularly be used well for the synthesis of important chiral compounds, particularly of (6R,10R)-6,10,14-trimethylpentadecan-2-one, (3RS,7R,11R)-3,7,11,15-tetramethylhexadec-1-en-3-ol), (2-ambo)-α-tocopherol or (2R,4'R,8'R)-α-tocopherol.

Furthermore, the above composition and the ketones or aldehydes, of formula (I-A) and (II-A) are very interesting for the use in the fields of pharma, food supplements and flavours and fragrances or as intermediate products in the synthesis of chiral substances, particularly for the synthesis of tocopherol or vitamin K1.

EXAMPLES

The present invention is further illustrated by the following experiments.

Analytical Methods

GC Determination of purity of (6R,10R)-6,10,14-trimethylpentadecan-2-one

Agilent 6850, column DB-5HT (30 m, 0.25 mm diameter, 0.10 μm film thickness), 115 kPa helium carrier gas). The samples were injected as solutions in hexane, split ratio 300:1, injector temperature 200° C., detector temperature 350° C. Oven temperature program: 120° C. (5 min), 14° C./min to 260° C. (2 min), 20° C./min to 280° C. (4 min), runtime 22 min.

(R)-6,10-dimethylundecan-2-one (THGA) and 6,10-dimethylundec-5-en-2-one (DHGA):

Agilent 6850, column DB-5HT (30 m, 0.25 mm diameter, 0.10 μm film thickness), 107 kPa helium carrier gas). The samples were injected as solutions in hexane, split ratio 300:1, injector temperature 200° C., detector temperature 350° C. Oven temperature program: 100° C. (8 min), 10° C./min to 200° C. (1 min), 20° C./min to 220° C. (4 min), runtime 24 min.

GC Determination of E/Z-ratio and/or purity of 6,10,14-trimethylpentadeca-5,9-dien-2-one (DHFA) and 6,10,14-trimethylpentadeca-5,9,13-trien-2-one (FA):

Agilent 6850 instrument, column Agilent DB-5 (123-5032E, 30 m×0.32 mm, film 0.25 µm), the samples were injected as solutions in acetonitrile, split ratio 50:1, injector 250° C., detector 350° C. Oven temperature program: 100° C., 4° C./min until 250° C., 37.5 min total runtime.

Retention time: EE-FA: 22.2 min; ZZ-FA: 21.0 min., EE-DHFR: 21.2 min., ZZ -DHFA:20.0 min. E-GA:11.0 min, Z-GA:10.6 min.

Analysis of the Asymmetrically Hydrogenated Reaction Products

The conversion of the hydrogenation reaction was determined by gas chromatography using an achiral column.

Method for Conversion:

Agilent 7890A GC equipped with FID. Agilent HP-5 column (30 m, 0.32 mm diameter, 0.25 µm film thickness) with 25 psi molecular hydrogen carrier gas. The samples were injected as solutions in dichloromethane with a split ratio of 10:1. Injector temperature: 250° C., detector temperature: 300° C. Oven temperature program: 50° C. (2 min) then 15° C./min to 300° C., hold 5 min.

For the determination of the isomer ratio, the hydrogenated ketones can be reacted with either (+)-diisopropyl-O,O'-bis(trimethylsilyl)-L-tartrate or (−)-diisopropyl-O,O'-bis(trimethylsilyl)-D-tartrate in the presence of trimethylsilyl triflate $[Si(CH_3)_3(OSO_2CF_3)]$ to form the diastereomeric ketals as described in A. Knierzinger, W. Walther, B. Weber, R. K. Müller, T. Netscher, *Helv. Chim. Acta* 1990, 73, 1087-1107. The ketals can be analysed by gas chromatography using an achiral column to determine the isomer ratios. For the hydrogenated ketone 6,10-dimethylundecan-2-one, either D-(−)- or L-(+)-diisopropyltartrate can be used. For 6,10,14-trimethylpentadecan-2-one, L-(+)-diisopropyltartrate can be used to measure the quantity of the (6R,10R)-isomer that was present. D-(−)-diisopropyltartrate can be used to determine the amount of the (6S,10S)-isomer. Thus the selectivity of the stereoselective hydrogenation can be determined indirectly.

Method for Determination of Isomers:

Agilent 6890N GC with FID. Agilent CP-Sil88 for FAME column (60 m, 0.25 mm diameter, 0.20 µm film thickness) with 16 psi molecular hydrogen carrier gas. The samples were injected as solutions in ethyl acetate with a split ratio of 5:1. Injector temperature: 250° C., FID detector temperature: 250° C. Oven temperature program: 165° C. (isothermal, 240 min)

The Ir complexes indicated in the following experiments are prepared according to the disclosure in *Chem. Sci.*, 2010, 1, 72-78.

Experiment E1: Separation of E/Z isomer mixtures of 6,10-dimethylundec-5-en-2-one 7.02 kg of 6,10-dimethylundec-5-en-2-one was prepared according to example 10 of DE 1 193 490 and was analyzed by the GC method given above to be a 57%/43% mixture of (E)-6,10-dimethylundec-5-en-2-one and (Z)-6,10-dimethylundec-5-en-2-one (99% purity).

The mixture was distilled using separation equipment consisting of a still (volume: 9 litre) with a falling film evaporator, a rectifying column (70 mm inner diameter, height 5 m). The column was equipped with a very efficient structured packing (Sulzer). The mixture was rectified at a top pressure of approx. 5 mbar and at a column top temperature in the range from 105 to 112° C. and a bottom temperature in the still of about 125° C. The reflux ratio was adjusted to 20.

Fractions containing (Z)-6,10-dimethylundec-5-en-2-one (content of Z-isomer=99%, E-isomer <1%)) ("Z-DHGA") as well as fractions containing (E)-6,10-dimethylundec-5-en-2-one (content of E-isomer 97%, Z-isomer <3%) ("E-DHGA") were collected. At the end (E)-6,10-dimethylundec-5-en-2-one (content of E-isomer=99.5%, Z-isomer=0.5%) was found left in the still.

Experiment E2: Separation of EE/ZZ/(EZ+ZE) isomer mixtures of 6,10,14-trimethylpentadeca-5,9,13-trien-2-one A commercial sample of 6,10,14-trimethylpentadeca-5,9,13-trien-2-one being a mixture of (5E,9E)-/ (5E,9Z)-/ (5Z,9E)-/ and (5Z,9Z)-6,10,14-trimethylpentadeca-5,9,13-trien-2-one has separated by fractional distillation into a low boiling fraction of the (5Z,9Z)-isomer and a high boiling fraction of (5E,9E) isomer and a mid boiling fraction containing both (5E,9Z)- and /(5Z,9E)-isomers.

The high boiling EE-isomer has been isolated as having a content of 97.9% of (5E,9E)-6,10,14-trimethylpentadeca-5,9,13-trien-2-one, 0% (5Z,9Z)-6,10,14-trimethylpentadeca-5,9,13-trien-2-one and 0.5% of the sum of (5E,9Z)- and (5Z,9E)-6,10,14-trimethylpentadeca-5,9,13-trien-2-one (total of 98.4% 6,10,14-trimethylpentadeca-5,9,13-trien-2-one isomers, measured by GC (labelled in the following as "EE-FA").

The low boiling ZZ-isomer has been isolated as having a content of 88.6% of (5Z,9Z)-6,10,14-trimethylpentadeca-5,9,13-trien-2-one, 0% (5E,9E)-6,10,14-trimethylpentadeca-5,9,13-trien-2-one and 4.0% of the sum of (5E,9Z)- and (5Z,9E)-6,10,14-trimethylpentadeca-5,9,13-trien-2-one (total of 92.6% 6,10,14-trimethylpentadeca-5,9,13-trien-2-one isomers, measured by GC) (labelled in the following as "ZZ-FA").

Experiment E3: Asymmetric Hydrogenations of Ketones in the Presence of Additives An autoclave vessel was charged under nitrogen with chiral iridium complex of formula (III-F) of the R configuration at the chiral centre marked by *, the ketone (conc.) as indicated in tables 1 to 5, solvent as indicated in tables 1 to 5 and an additive as indicated in tables 1 to 5. The reaction vessel was closed and pressurized with molecular hydrogen to the pressure ($pH_2$) indicated in tables 1 to 5. The reaction mixture was stirred at room temperature for the time (t) as indicated in tables 1 to 5 under hydrogen. Then the pressure was released and the assay yield and the stereoisomer distribution of the fully hydrogenated product was determined. The catalyst loading (S/C) is defined as mmol ketone ("substrate")/mmol chiral iridium complex.

The additives tetraisopropyl orthotitanate ($Ti(OiPr)_4$), aluminium triisopropoxide ($Al(OiPr)_3$), tri-isopropylborate ($B(OiPr)_3$), yttrium triflate ($Y(OTf)_3$), scandium triflate ($Sc(OTf)_3$), sodium tetrakis[3,5-bis(trifluoromethyl)phenyl]borate ($NaBAr_F$), trimethylaluminum (TMA) and triethyl borane (TEB) (1 M solution in hexane) are commercially available and were used as received.

Triflic acid was introduced in the hydrogenation experiments as a freshly prepared 0.1 M solution in dichloromethane.

MAO/TFE: A 1.6 M MAO (MAO: methylaluminoxane solution in toluene (0.64 mL) was quenched with 2,2,2-trifluorethanol (TFE) (3.1 mmol), leading to small excess of free TFE.

EAO/TFE: A 10 wt % EAO (EAO: ethylaluminoxane solution in toluene (1 mmol) was quenched with TFE (3.2 mmol), leading to small excess of free TFE.

TMA/TFE: A 2 M TMA (TMA: trimethylaluminum (Al(CH$_3$)$_3$)) solution in heptane (1 mmol) was quenched with TFE (3.1 mmol), leading to small excess of free TFE.

Ti(OCH$_2$CF$_3$)$_4$: Tetraisopropyl orthotitanate (8.1 mmol) was dissolved in 2,2,2-trifluoroethanol at 50° C. Removal of the solvent gave Ti(OCH$_2$CF$_3$)$_4$ as a white residue which was isolated and identified to be Ti(OCH$_2$CF$_3$)$_4$.

These additives were freshly prepared and used either as a heterogeneous mixture at room temperature or homogeneous by heating to a temperature between 50° and 70° C.

TABLE 1

Hydrogenation of E-DHGA at pressure of molecular hydrogen (pH$_2$) of 50 bar and stirring at room temperature during 20 hours. The effect of the additives.

|  | Ref. 1 | 1 | 2 | 3 | 4 |
|---|---|---|---|---|---|
| Ketone to be hydrogenated | E-DHGA- | E-DHGA- | E-DHGA | E-DHGA | E-DHGA |
| conc.[1] [mol/L] | 1.0 | 0.8 | 0.2 | 0.2 | 0.9 |
| S/C | 10'000 | 10'000 | 10'000 | 10'000 | 10'000 |
| Solvent | TFE | TFE | TFE | TFE | TFE |
| Additive | — | TMA/TFE | TMA/TFE | MAO/TFE | Ti(OiPr)$_4$ |
| Additive concentration [mol-%][2] | — | 5 | 5 | 10 | 10 |
| Assay yield [area-%] | 1 | 73 | 78 | 53 | 90 |
| (R)-6,10-dimethylundecan-2-one [%] | n.d.[3] | 2.8 | 2.3 | 4.2 | 2.2 |
| (S)-6,10-dimethylundecan-2-one [%] | n.d.[3] | 97.2 | 97.7 | 95.8 | 97.8 |

[1]conc. = mol ketone/L solvent
[2]relative to the molar amount of E-DHGA.
[3]n.d. = not determined (due to low assay yield).

TABLE 2

Hydrogenation of Z-DHGA at pressure of molecular hydrogen (pH$_2$) of 50 bar and stirring at room temperature during 20 hours. The effect of additives.

|  | Ref. 2 | 5 |
|---|---|---|
| Ketone to be hydrogenated | Z-DHGA | Z-DHGA |
| conc.[1] [mol/L] | 1.0 | 0.8 |
| S/C | 5'000 | 5'000 |
| Solvent | DCM | DCM |
| Additive | — | TMA/TFE |
| Additive concentration [mol-%][2] | — | 5 |
| Assay yield [area-%] | 1 | 40 |
| (R)-6,10-dimethylundecan-2-one [%] | n.d.[3] | 98.3 |
| (S)-6,10-dimethylundecan-2-one [%] | n.d.[3] | 1.7 |

[1]conc. = mol ketone/L solvent
[2]relative to the molar amount of Z-DHGA.
[3]n.d. = not determined (due to low assay yield).

TABLE 3

Hydrogenation of EE-FA (0.2M in 2,2,2-trifluorethanol (TFE) and stirring at room temperature during 20 hours. The effect of the additives.

|  | Ref. 3 | 6 | 7 | 8 | 9 |
|---|---|---|---|---|---|
| Ketone to be hydrogenated | EE-FA | EE-FA | EE-FA | EE-FA | EE-FA |
| S/C | 1000 | 1000 | 2000 | 2000 | 2000 |
| Solvent | TFE | TFE | TFE | TFE | TFE |
| Additive | — | Triflic acid | Al(OiPr)$_3$ | TEA | Ti(OiPr)$_4$ |
| Additive concentration [mol-%][1] | — | 1 | 10 | 10 | 7 |
| Pressure of H$_2$ [bar] | 25 | 25 | 25 | 25 | 25 |
| Assay yield [area-%] | 21 | 98 | 94 | 72 | 93 |
| Isomer-Distribution[2] |  |  |  |  |  |
| (RS) [%] | 8.4 | 2.3 | 4.1 | 2.1 | 2.4 |
| ((RR) + (SR)) [%] | 4.1 | 1.6 | 1.5 | 1.3 | 1.5 |
| (SS) [%] | 87.5 | 96.1 | 94.4 | 96.6 | 96.1 |

[1]relative to the molar amount of EE-FA
[2](SS) stands for the (6S,10S)-isomer, (RR) stands for the (6R,10R)-isomer, (SR) stands for the (6S,10R)-isomer, (RS) stands for the (6R,10S)-isomer of 6,10,14-trimethylpentadecan-2-one.

TABLE 4

Hydrogenation of EE-FA (0.2M in 2,2,2-trifluorethanol (TFE) and stirring at room temperature during 20 hours. The effect of the additives.

|  | 10 | 11 | 12 | 13 | 14 |
|---|---|---|---|---|---|
| Ketone to be hydrogenated | EE-FA | EE-FA | EE-FA | EE-FA | EE-FA |
| S/C | 2000 | 2000 | 2000 | 2000 | 2000 |
| Solvent | TFE | TFE | TFE | TFE | TFE |
| Additive | $Y(OTf)_3$ | $Sc(OTf)_3$ | $Ti(OCH_2CF_3)_4$ | MAO/TFE | TMA/TFE |
| Additive concentration [mol-%][1] | 0.25 | 0.1 | 14 | 10 | 5 |
| Pressure of $H_2$ [bar] | 25 | 25 | 25 | 50 | 50 |
| Assay yield [area-%] | 84 | 79 | 90 | 78 | 92 |
| Isomer-Distribution[2] | | | | | |
| (RS) [%] | 3.5 | 3.2 | 2.6 | 2.8 | 3.1 |
| ((RR) + (SR)) [%] | 2.5 | 1.9 | 1.6 | 2.2 | 2.1 |
| (SS) [%] | 94.0 | 94.9 | 95.8 | 95.0 | 94.8 |

[1] relative to the molar amount of EE-FA
[2] (SS) stands for the (6S,10S)-isomer, (RR) stands for the (6R,10R)-isomer, (SR) stands for the (6S,10R)-isomer, (RS) stands for the (6R,10S)-isomer of 6,10,14-trimethylpentadecan-2-one.

TABLE 5

Hydrogenation of ZZ-FA (0.2M in 2,2,2-trifluorethanol (TFE) and stirring at room temperature during 20 hours. The effect of the additives.

|  | Ref. 4 | 15 | 16 |
|---|---|---|---|
| Ketone to be hydrogenated | ZZ-FA | ZZ-FA | ZZ-FA |
| S/C | 2000 | 2000 | 2000 |
| Solvent | TFE | TFE | TFE |
| Additive | — | $Y(OTf)_3$ | $Ti(OiPr)_4$ |
| Additive concentration [mol-%][1] | — | 0.2 | 14 |
| Pressure of $H_2$ [bar] | 50 | 50 | 50 |
| Assay yield [area-%] | 9 | 76 | 53 |
| Isomer-Distribution[2] | | | |
| (RR) [%] | 89.9 | 92.8 | 91.8 |
| ((SS) + (RS)) [%] | 5.0 | 3.4 | 3.9 |
| (SR) [%] | 5.1 | 3.8 | 4.3 |

[1] relative to the molar amount of ZZ-FA
[2] (SS) stands for the (6S,10S)-isomer, (RR) stands for the (6R,10R)-isomer, (SR) stands for the (6S,10R)-isomer, (RS) stands for the (6R,10S)-isomer of 6,10,14-trimethylpentadecan-2-one.

The invention claim is:

1. A process of manufacturing compound of formula (I-A) or (II-A) which comprises conducting asymmetric hydrogenation of an unsaturated ketone or unsaturated aldehyde of the formula (I) or (II) with molecular hydrogen in the presence of at least one chiral iridium complex and in the presence of at least one additive and 2,2,2-trifluoroethanol:

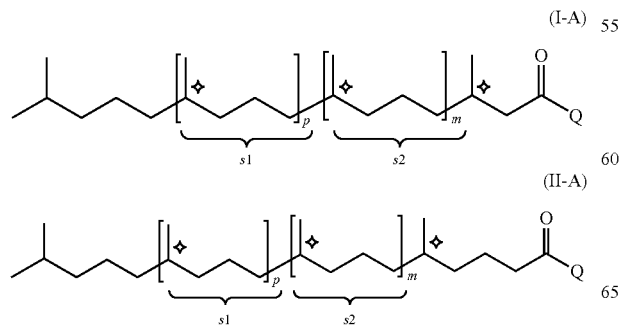

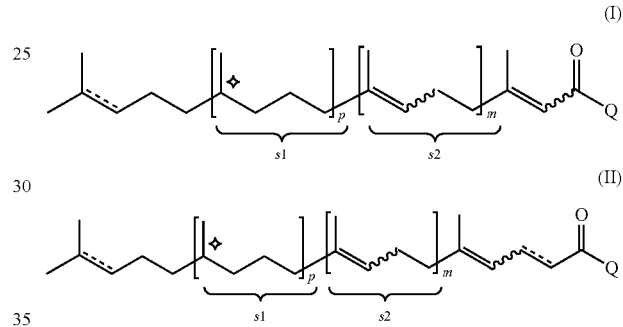

wherein Q stands for H or $CH_3$ and m and p stand independently from each other for a value of 0 to 3 with the proviso that the sum of m and p is 0 to 3, and wherein a wavy line represents a carbon-carbon bond which is linked to the adjacent carbon-carbon double bond so as to have said carbon-carbon double bond either in the Z or in the E-configuration and where the substructures in formula (I) and (II) represented by s1 and s2 can be in any sequence; and wherein the double bond having dotted line ( ===== ) in formula (I) and (II) represents either a single carbon-carbon bond or a double carbon-carbon bond;

and wherein ✧ represents a stereogenic centre; and wherein the additive is selected from the group consisting of organic sulfonic acids, transition metal salts of organic sulfonic acids, metal alkoxides, aluminoxanes, alkyl aluminoxanes and $B(R)_{(3-v)}(OZ)v$;

wherein v stands for 0, 1, 2 or 3;

R stands for F, a $C_{1-6}$-alkyl, a halogenated $C_{1-6}$-alkyl, an aryl or halogenated aryl group; and Z stands for a $C_{1-6}$-alkyl, a halogenated $C_{1-6}$-alkyl, an aryl or a halogenated aryl group.

2. The process according to claim 1 wherein the chiral iridium complex is an iridium complex having ligands bound to the iridium central atom and that exactly one of the ligands is an organic ligand bearing a stereogenic centre.

3. The process according to claim 1 wherein the chiral iridium complex has the formula (III):

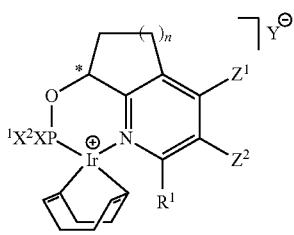

(III)

wherein
n is 1, 2 or 3;
$^1X$ and $^2X$ are independently from each other hydrogen atoms, $C_{1-4}$-alkyl, $C_{5-7}$-cycloalkyl, adamantyl, phenyl optionally substituted with one to three $C_{1-5}$-alkyl, $C_{1-4}$-alkoxy, $C_{1-4}$-perfluoroalkyl groups and/or one to five halogen atoms, benzyl, 1-naphthyl, 2-naphthyl, 2-furyl or ferrocenyl;
$Z^1$ and $Z^2$ are independently from each other hydrogen atoms, $C_{1-5}$-alkyl or $C_{1-5}$-alkoxy groups; or $Z^1$ and $Z^2$ stand together for a bridging group forming a 5 or 6 membered ring;
$Y^\ominus$ is an anion selected from the group consisting of halide, $PF_6^-$, $SbF_6^-$, tetra(3,5-bis(trifluoromethyl)phenyl)borate($Bar_F^-$), $BF_4^-$, perfluorinated sulfonates; $ClO_4^-$, $Al(OC_6F_5)_4^-$, $Al(OC(CF_3)_3)_4^-$, $^-N(SO_2CF_3)_2$ $^-N(SO_2C_4F_9)_2$ $^-$ and $B(C_6F_5)_4^-$;
$R^1$ represents either phenyl or o-tolyl or m-tolyl or p-tolyl or a group of formula (IVa) or (IVb) or (IVc):

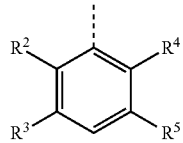

(IVa)

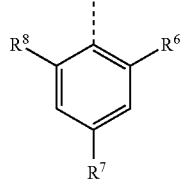

(IVb)

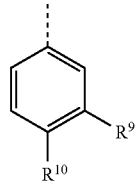

(IVc)

wherein $R^2$ and $R^3$ represent either both H or a $C_1$-$C_4$-alkyl group or a halogenated $C_1$-$C_4$-alkyl group or represent a divalent group forming together a 6-membered cycloaliphatic or an aromatic ring which optionally is substituted by halogens atoms or by $C_1$-$C_4$-alkyl groups or by $C_1$-$C_4$-alkoxy groups $R^4$ and $R^5$ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogens atoms or by $C_1$-$C_4$-alkyl groups or by $C_1$-$C_4$-alkoxy groups;

$R^6$ and $R^7$ and $R^8$ represent each a $C_1$-$C_4$-alkyl group or a halogenated $C_1$-$C_4$-alkyl group;

$R^9$ and $R^{10}$ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogens atoms or by $C_1$-$C_4$-alkyl groups or by $C_1$-$C_4$-alkoxy groups;

and wherein * represents a stereogenic centre of the complex of formula (lll).

4. The process according to claim 1 wherein the chiral iridium complex is present during the hydrogenation in an amount in the range from 0.0001 to 5 mol %, based on the amount of the unsaturated ketone or unsaturated aldehyde of the formula (I) or (II).

5. The process according to claim 1 wherein the compound of formulas (I) or (II) is selected from the group consisting of 3,7-dimethyloct-6-enal, 3,7-dimethylocta-2,6-dienal, 3,7-dimethyloct-2-enal, 6,10-dimethylundeca 3,5,9-trien-2-one, 6,10-dimethylundeca-5,9-dien-2-one, 6,10-dimethylundec-5en-2-one, 6,10-dimethylundec-3-en-2-one, 6,10-dimethylundec-3,5-diene-2-one, 6,10,14-trimethylpentadeca-5,9,13-trien-2-one, 6,10,14-trimethylpentadeca-5,9-dien-2-one, 6,10,14-trimethylpentadec-5-en-2-one and E/Z-isomers thereof.

6. The process according to claim 1 wherein the additive is selected from the group consisting of triflic acid, methyl aluminoxane, ethyl aluminoxane, tetra alkoxy titanates, triisopropylborate, triethylborane, and $BF_3$ etherate.

7. The process according to claim 1 wherein the additive is present in the range of 1 to 3000 mol additive per mol chiral iridium complex.

8. The process according to claim 1, wherein the additive is selected from the group consisting of trimethylaluminoxane and trialkyaluminum.

* * * * *